United States Patent
Zografos et al.

(10) Patent No.: US 11,699,045 B2
(45) Date of Patent: *Jul. 11, 2023

(54) PRODUCT TRACKING AND RATING SYSTEM USING DNA TAGS

(71) Applicant: SafeTraces, Inc., Pleasanton, CA (US)

(72) Inventors: Antonios Zografos, Oakland, CA (US); Laurie M. Clotilde, Hayward, CA (US)

(73) Assignee: SafeTraces, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/544,828

(22) Filed: Dec. 7, 2021

(65) Prior Publication Data

US 2022/0245367 A1 Aug. 4, 2022

Related U.S. Application Data

(63) Continuation of application No. 16/554,294, filed on Aug. 28, 2019, now Pat. No. 11,200,383.
(Continued)

(51) Int. Cl.
*G06K 7/00* (2006.01)
*G06K 7/12* (2006.01)
(Continued)

(52) U.S. Cl.
CPC ....... *G06K 7/0004* (2013.01); *G06K 7/10366* (2013.01); *G06K 7/12* (2013.01); *G16B 50/10* (2019.02)

(58) Field of Classification Search
CPC .... G06K 7/0004; G06K 7/10366; G06K 7/12; G16B 50/10
See application file for complete search history.

(56) References Cited

U.S. PATENT DOCUMENTS

| 4,593,360 A | 6/1986 | Cocks |
| 6,312,911 B1 | 11/2001 | Bancroft et al. |

(Continued)

FOREIGN PATENT DOCUMENTS

| CN | 101379188 A | 3/2009 |
| CN | 104024426 A | 9/2014 |

(Continued)

OTHER PUBLICATIONS

Andrews, "DNA Spray-On Technology Could Revolutionize Food Traceability," Food Safety News, http://www.fooodsafetynews.com/2014/11/dna-laced-spray-technology-could-revolutionize-food-traceability/#.W1kRNNVKjRY, Nov. 17, 2014, 2 pages.
(Continued)

*Primary Examiner* — Seung H Lee
(74) *Attorney, Agent, or Firm* — Haynes and Boone, LLP

(57) ABSTRACT

Material in a supply chain is tracked by a method of applying a DNA taggant set to a first batch of the material produced by a first supplier of the material. The DNA taggant set corresponds to a tag string corresponding to the first supplier. The first batch is aggregated with a second batch to create an aggregated lot. A sample is selected from the aggregated lot and tested to determine a DNA taggant set of the sample. After selecting a sample from the aggregated lot, the sample may be labeled with a grade and then placed in a receptacle corresponding to the grade.

19 Claims, 7 Drawing Sheets

Related U.S. Application Data

(60) Provisional application No. 62/870,011, filed on Jul. 2, 2019, provisional application No. 62/723,974, filed on Aug. 28, 2018.

(51) Int. Cl.
    *G06K 7/10*     (2006.01)
    *G16B 50/10*     (2019.01)

(56) References Cited

U.S. PATENT DOCUMENTS

| | | |
|---|---|---|
| 8,293,535 B2 | 10/2012 | Farquar et al. |
| 8,735,327 B2 | 5/2014 | Macula |
| 10,962,512 B2 | 3/2021 | Zografos et al. |
| 11,200,383 B2 * | 12/2021 | Zografos .............. G16B 50/10 |
| 2002/0129523 A1 | 9/2002 | Hunt |
| 2004/0166520 A1 | 8/2004 | Connolly |
| 2006/0037222 A1 | 2/2006 | Hunt et al. |
| 2010/0261193 A1 | 10/2010 | Webster et al. |
| 2011/0177539 A1 | 7/2011 | Sutton et al. |
| 2012/0112883 A1 | 5/2012 | Wallace et al. |
| 2013/0052751 A1 | 2/2013 | Farquar et al. |
| 2013/0122807 A1 | 5/2013 | Fenarvitz et al. |
| 2014/0057276 A1 | 2/2014 | Farquar et al. |
| 2014/0220576 A1 | 8/2014 | Macula |
| 2014/0255984 A1 | 9/2014 | Sharpin |
| 2014/0272097 A1 | 9/2014 | Jung et al. |
| 2014/0340423 A1 | 11/2014 | Taylor et al. |
| 2015/0104802 A1 | 4/2015 | Reep et al. |
| 2015/0361490 A1 | 12/2015 | Farquar et al. |
| 2016/0102335 A1 | 4/2016 | Franciskovich et al. |
| 2016/0171179 A1 | 6/2016 | Donofrio et al. |
| 2016/0188943 A1 | 6/2016 | Franz |
| 2017/0197002 A1 | 7/2017 | Dobrinsky et al. |
| 2017/0322701 A1 | 11/2017 | Bowman et al. |
| 2017/0333859 A1 | 11/2017 | Lind |
| 2018/0252738 A1 | 9/2018 | Denney |
| 2019/0338354 A1 | 11/2019 | Gonzales, Jr. |
| 2020/0385824 A1 | 12/2020 | Hogan et al. |

FOREIGN PATENT DOCUMENTS

| | | |
|---|---|---|
| CN | 104131008 A | 11/2014 |
| CN | 104513863 A | 4/2015 |
| WO | 2008137831 A1 | 11/2008 |
| WO | 2011163296 A2 | 12/2011 |
| WO | 2012037876 A1 | 3/2012 |
| WO | 2014164958 A1 | 10/2014 |

OTHER PUBLICATIONS

Busta et al., "The Use of Indicators and Surrogate Microorganisms for the Evaluation of Pathogens in Fresh and Fresh-Cut Produce," Comprehensive Reviews in Food Science and Food Safety, 2(s1), Jan. 2003, pp. 179-185.

Bystrykh, "Generalized DNA Barcode Design Based on Hamming Codes," PLOS One 7(5):e36852, May 17, 2012, 8 pages.

Danyluk et al., "Process Validation: Selection and Use of Surrogates," University of Florida Institute of Food and Argicultural Sciences, presentation dated Apr. 2014, 19 pages.

Extended European Search Report dated Feb. 26, 2019, European Patent Application No. 16833458.9, filed Jun. 17, 2016, 5 pages.

Farquar, "DNATrax (DNA Tagged Reagents for Aerosol experiments)," Lawrence Livermore National Laboratory, presentation LLNL-PRES-642415, Aug. 2013, retrieved from the internet at <http://web.archive.org/web/20160226230017/https:/lipo.llnl.gov/technologies/individual-tech-discoveryp=DNATrax>, 6 pages.

Harding et al., "Unique DNA-barcoded aerosol test particles for studying aerosol transport," Aerosol Science and Technology 50(5):429-435, Mar. 22, 2016.

Hou et al., "Rapid bioparticle concentration and detection by combining a discharge driven vortex with surface enhanced Raman scattering," Biomicrofluids 1.014106:1-13, Feb. 16, 2007.

International Search Report and Written Opinion dated Aug. 8, 2019, International Patent Application No. PCT/US2019/029002, filed Apr. 24, 2019, 8 pages.

International Search Report and Written Opinion dated Sep. 8, 2016, International Patent Application No. PCT/US2016/038083, filed Jun. 17, 2016.

International Search Report and Written Opinion, dated Mar. 15, 2019, International Patent Applicaton No. PCT/US19/13069, filed Jan. 10, 2019, 13 pages.

Ma et al., "Development of Thermal Surrogate Microorganisms in Ground Beef for In-Plant Critical Control Point Validation Studies," Journal of Food Protection, 70(4), Apr. 2007, pp. 952-957.

Naaum, "Novel Methods of Species and Product Authenticity and Traceability Testing Using DNA Analysis for Food and Agricultural Applications," Doctoral Dissertation, Department of Integrative Biology University of Guelph, Apr. 2014, 144 pages.

Niebuhr et al., "Evaluation of non-pathogenic surrogate bacteria as process validation indicators for *Salmonella enteric* for selected antimicrobial treatments, cold storage and fermentation in meat," Journal of Food Protection, 71(4), Apr. 2008, pp. 714-718.

Oxford Gene Technology, "DNA Storage and Quality," Aug. 2011 [retrieved Oct. 30, 2018 https://www.pgt.com/resources/literature/403_dna_storage_and_quality, 5 pages.

Puddu et al., "Magnetically Recoverable, Thermostable, Hydrophobic DNA/Silica Encapsulates and Their Application as Invisible Oil Tags," ACS Nano 8(3):2677-2685, Feb. 25, 2014.

Sharma et al., "Hydrological Tracers Using Nanobiotechnology: Proof of Concept," Environmental Science and Technology, 46(16):8928-8936, Aug. 21, 2012.

Sinclair et al., "A Criteria for Selection of Surrogates Used to Study the Fate and Control of Pathogens in the Environment," Applied and Environmental Microbiology, 78(6), published online Jan. 13, 2012, published in print Mar. 2012, pp. 1969-1977.

Yeater et al., "Effectiveness of Sanitzing Products on Controlling Selected Pathogen Surrogates on Retail Deli Slicers," Journal of Food Protection, 78(4), Apr. 2015, pp. 707-715.

\* cited by examiner

PRODUCT TRACKING AND RATING SYSTEM USING DNA TAGS

CROSS-REFERENCES TO RELATED APPLICATIONS

This application is a continuation of U.S. patent application Ser. No. 16/554,294, filed Aug. 28, 2019, entitled "Product Tracking and Rating System Using DNA Tags".

This application incorporates by reference the entire disclosures of the following application(s)/patent(s), as if set forth in full in this document, for all purposes:

1) U.S. Provisional Patent Application No. 62/723,974, filed Aug. 28, 2018, entitled, "Product Tracking and Rating System Using DNA Tags";

2) U.S. Provisional Patent Application No. 62/870,011, filed Jul. 2, 2019, entitled "Product Tracking and Rating System Using DNA Tags";

3) U.S. Pat. No. 10,302,614, issued May 28, 2019, entitled "DNA Based Bar Code for Improved Food Traceability" issued to Zografos et al. ("Zografos I"); and 4) U.S. patent application Ser. No. 15/867,441, filed Jan. 10, 2018, entitled "Dispensing System for Applying DNA Taggants Used in Combinations to Tag Articles" issued to Zografos, et al. ("Zografos II").

FIELD OF THE INVENTION

The present disclosure generally relates to facilitating the tracking of a substance as it moves through a supply chain. The disclosure relates more particularly to apparatus and techniques for using DNA sequences for tracking a food material and identifying a food material by source after the food material has been aggregated with other, similar food materials.

BACKGROUND

Techniques for detecting sequences of DNA are known. In some approaches, a sample is prepared and an analysis process is applied to the sample to cause any DNA in the sample to replicate many times, sufficient for other processes to identify that a particular DNA sequence was present in the sample. For example, if the sample is from a person, the DNA of the sample might be replicated and then the result tested for the presence or lack of presence of a DNA sequence that is unique to a particular person with some probability. In this manner, a sample might be matched to a person, within some probability.

This analysis process is useful for determining whether a particular species is present in a food or agricultural application. For example, there might be a DNA sequence that is unique to a species of nuts and the analysis can replicate the DNA of a sample, including the endogenous DNA of the nuts, sufficient to determine whether or not the sample contained any of those nuts.

In other variations, a DNA sequence that is not endogenous to contents of the sample might be added. For example, synthetic oligonucleotides can be added to a food product to allow that food product to be traced from a source where the oligonucleotides were added to the point where an analysis is done. The analysis, i.e., sampling, replicating, analyzing, would then be able to determine whether or not the food product being tested came from that source. In either case, this requires considerable coordination, as an analysis system would have to be aware of all of the possible synthetic oligonucleotides that are being tested for. If there are, say, thousands of sources, the sampling and analysis for each of those thousand sources can be difficult.

Zografos I describes how a set of independent DNA taggants might be used to tag a food product or other item with a bit pattern by having each DNA taggant in the set of independent DNA taggants represent a bit in the bit pattern. Using that approach, N or 2N unique identifiers can be used and discerned with only N or 2N sampling steps needed, while allowing for up to $2^N$ unique identifiers with those taggants. In some approaches, the presence of a particular DNA taggant set represents a "1" and the absence of that particular DNA taggant set represents a "0" (the case where of the N taggants, each is used or not used) or the presence of a second particular DNA taggant set represents a "0" (the case where, of 2N taggants, N are used). Each set of taggants of the DNA taggants in the taggant set is preferably such that they are biologically inert so as to not interfere with their consumption as part of a food product.

Zografos II describes a dispensing system for DNA taggants. The system comprises a plurality of taggant vessels, each having a taggant corresponding to a position in a tag string. A computer controller converts the tag string into a selection of a taggants by using valves to allow or block the flow of taggants to a manifold output tube. From the output tube, a mix of the taggants flow to form a dispersant formed according to the tag string. A nozzle disperses the dispersant onto an object to be tagged, possibly atomized with air or mixed with a carrier fluid, such as ethanol. The taggant can comprise a DNA taggant comprising a static portion and a dynamic portion that is unique to each tag string position.

Multiple sources may produce similar food products that are aggregated together for shipping or manufacturing. By the time the food product reaches a user, it may be impossible to ascertain which component lot of a larger shipment came from which supplier. The suppliers may produce products having different levels of quality, but rating the food product by provider may be impossible after aggregation. A method of distinguishing a food product's source after aggregation would be beneficial.

SUMMARY

A method tracks material in a supply chain by applying a DNA taggant set to a first batch of the material produced by a first supplier of the material. A DNA taggant set might comprise one or more DNA taggants selected from among a plurality of DNA taggants wherein an association is recorded between which DNA taggants are selected and particular values in particular positions in a tag string that the DNA taggant set is intended to represent. In a specific example, a tag string is a binary string that can be represented by N bits each having one of N positions in the tag string and the DNA taggant set that is associated with a particular tag string comprises an aggregation of DNA taggants selected from among a plurality of N DNA taggants, with a value of a given bit of the tag string represented by whether or not the aggregation includes the DNA taggant associated with that given bit. A DNA taggant might be a small DNA sequence that is genetically inactive, but identifiable and a DNA taggant set might comprise a plurality of selected DNA taggants that are aggregated but need not be combined such that all of the DNA taggants in the set form a single DNA chain and instead could be an aggregation of unconnected DNA snippets.

When used for tracking suppliers, the DNA taggant set can correspond to a tag string that is associated with the first supplier. A sample can be taken from batch of material and tested to determine a DNA taggant set used on that material, and in checking with prerecorded associations of DNA taggant selections and suppliers, the supplier of the sample can be easily identified.

The DNA taggant set may be applied by applying, for example, by spraying, the DNA taggant of the taggant set onto the batch of the material with an applicator, such as, for example, a sprayer, that might be capable of applying multiple DNA taggant sets. The DNA taggants may be selected from many DNA taggants to determine the DNA taggant set. After applying the DNA taggant set to the first batch of material, a second DNA taggant set may be selected and applied to a second batch. After selecting a sample from an aggregated lot comprising the first batch and the second batch, the sample may be labeled with a grade and then placed in a receptacle corresponding to the grade, wherein the grade is represented by a previously recorded association with the batch. At a different location, the graded sample may be tested to determine the DNA taggant set.

The DNA taggant set may comprise a taggant material including at least N unique DNA snippets used as taggants, representing N digits of a tag string that identifies the batch of the material, N being a positive integer greater than 1, wherein each of the at least N unique of DNA snippets represents one value of a corresponding one of the N digits of the tag string. The tag string could be recorded in a database, on paper, or using some formula, or using other methods, so as to associate a tag string with other information, such as a particular supplier. The DNA snippets applied to the item may be detected to derive a bar code that is compared to a predetermined bar code to identify the first batch. The DNA bar code may include at least N unique specific target fragments of synthetic DNA, wherein each of the at least N unique specific target fragments of synthetic DNA corresponds to a binary value of zero or a binary value of one. In some implementations, a tag string comprises N characters, where N is greater than one, each character having a position and having one of M values, allowing for up to $N^M$ distinct tag strings and a DNA taggant set associated with a specific tag string comprises a selection of DNA taggants selected by selecting, for each of the N characters, a DNA snippet associated with the value of that character. In some cases, the DNA snippets are selected from among N*M available snippets, but might also be selected from among N*(M−1) snippets in cases where one of the M values for a character is represented by an absence of any of the other DNA taggants associated with the other M−1 possible values for that character.

Associations indicating which DNA snippet sequence corresponds to which character position in a tag string and which character value at that position might be stored in a database that is publicly available or not publicly available. Associations indicating which suppliers are associated with which tag strings might be stored in a database that is publicly available or not publicly available. In other variations, associations might be algorithmically defined. In one specific example, N=28, M=2 and a database is maintained that stores associations of up to $2^{28}$ tag strings with individual supplier identities. In another specific example, N=100, M=36 and each tag string comprises up to 100 alphabetic characters directly identifying names of suppliers. In yet another specific example, a tag string is usable as a blockchain address and in that manner identifies a supplier that is using the DNA taggant set that corresponds to that tag string.

By controlling how an applicator, such as, for example, a sprayer, is used, how much taggant is dispersed per application, how many applications are allotted, geofencing use of applicators, such as sprayers, and other techniques, a supply chain can be monitored, products and material can be graded, and other operations are possible from identifying DNA taggant sets in samples of product or material.

The following detailed description together with the accompanying drawings will provide a better understanding of the nature and advantages of the present invention.

BRIEF DESCRIPTION OF THE DRAWINGS

Various embodiments in accordance with the present disclosure will be described with reference to the drawings, in which.

DETAILED DESCRIPTION

Figure 1:
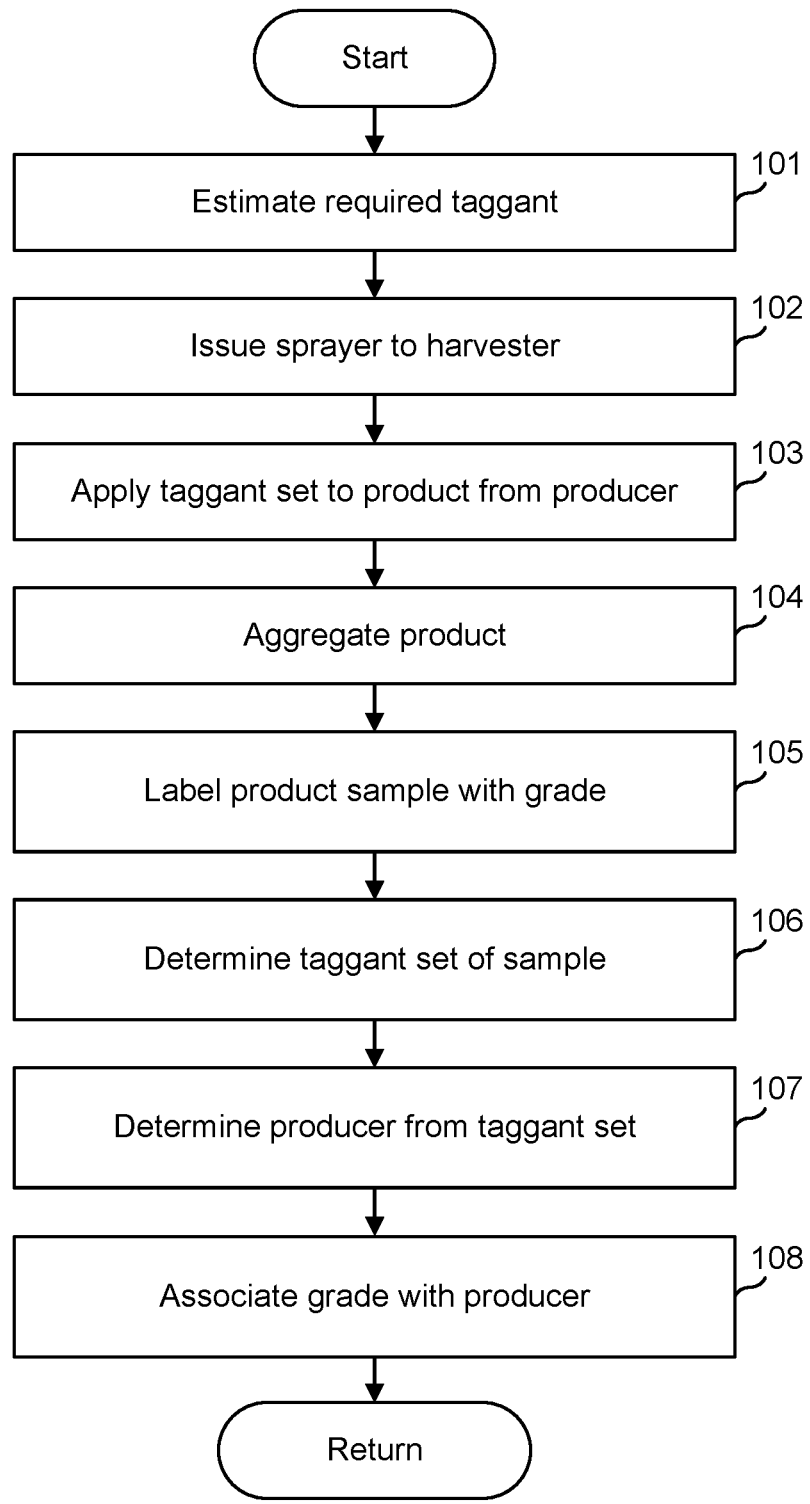
FIG. 1 is a flowchart illustrating a method of tagging a product to indicate the producer of the product.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Techniques described and suggested herein include methods and apparatus to apply DNA taggants to batches of material from different producers before the batches are transported to a processing facility, allowing the processing facility to verify the producer of a particular unit of the material to be identified. The techniques, methods, and apparatus described and suggested herein are applicable to products in general, and particularly to agricultural products.

An illustrative application is in the production of palm oil, produced from the fruit of oil palms. In a world hungry for oil, the oil palm tree (*Elaeis guineensis*) remains a top producer, yielding up to nine times as much per acre as other vegetable oil crops. This exceptional productivity—paired with palm oil's remarkable versatility—has given rise over only a few decades to an extensive patchwork of large plantations and small holder producers. Palm and palm kernel oil now provides nearly 40% of the world's vegetable oils and fats since circa 2015, making it the world's most widely used vegetable oil. The resulting palm oil, palm kernel oil, and derivatives flow through vast supply chains that produce such everyday items as processed food (72%), cosmetics, household/cleaning, and personal care products (18%), and as feedstock and biofuel additives (10%) for many prominent brands. Palm oil and its derivatives are present in major brands, with current global consumption for all products at circa 8 kg per capita. In 2018, production grew to 77 million tonnes, and growth is projected at 1.7% per year until 2050.

Unfortunately, there is a history of environmental and labor abuse in the palm oil supply chain. Further, palm oil production raises global environmental concerns. To keep pace with growing demand, large expanses of tropical forests have been—and continue to be—logged and/or slashed and burned to make way for oil palm cultivation, primarily in Indonesia and Malaysia. While this has created economic opportunity for some, serious negative environmental and social consequences affect many Massive deforestation is directly linked to indigenous land rights violations, community displacement, species extinction, accelerated climate change, and air pollution levels due to smoke that are among the highest on record.

Once established, oil palm plantations create jobs. However, reports of forced labor, lack of worker protection from harmful chemicals, and lack of basic employment benefits and security for targeted populations put a spotlight on practices that create concern within certain market sectors.

Demand for products that are sustainably and ethically sourced continues to grow. The global market value of ethically labeled packaged food products and beverages amounted to about 794 billion U.S. dollars in 2015 and is expected to reach nearly 873 billion in 2020. Sustainably sourced palm oil is no exception, and lack of assurances can cause market sectors to contract. A case in point is the 2019 European Union (EU) decision to put a cap on subsidies for palm oil use in biodiesel; a governing body's review of the consequences of palm oil cultivation determined that palm oil use for fuel is environmentally unsustainable.

Addressing the wide range of sustainability issues associated with the palm oil industry demands a rapid departure from "business as usual." The Indonesian government has already started placing restrictions on burning tropical forests, particularly those rooted in carbon-rich layers of peat. Norway is incentivizing this with financial compensation, provided the Indonesian government can demonstrate an overall reduction in deforestation. Satellite imaging helps verify that these sustainability goals are being met. Soon, palm growers may need to demonstrate a deeper commitment to sustainability goals, and an innovative system that includes satellite imaging, geo-location of the harvest site, and on-product DNA barcodes can provide that assurance.

The palm oil industry has understood that establishing sustainability guidelines would benefit it as a whole, since at least 2004. That year, the World Wildlife Fund (WWF) and industry leaders formed the Roundtable for Sustainable Palm Oil (RSPO), a voluntary membership organization that now has more than 4,000 members worldwide. Membership has grown to represent the entire palm oil supply chain as well as advocates for the environment, land ownership, and worker's rights. Much has been accomplished through these partnerships, but particularly with the impacts of climate change in the news nearly every day, more stringent sustainability assurance from consumers and governments is sure to follow. Technologies at the leading edge can help meet this challenge.

RSPO is the primary organization that sets criteria for sustainability certification for the global palm oil industry. While parallel certifying bodies focus on specific issues or offer specialized services, RSPO continues to be the internationally recognized label for sustainability assurance. Criteria include upholding requirements for ensuring ecosystem protection, incorporating buffer zones for wildlife, safeguarding worker safety and health, and implementing best practices to increase yield while reducing the use of pesticides and herbicides.

In 2018, nearly 20% of the global oil palm crop qualified to carry the RSPO certified sustainable label. The WWF has noted that achieving RSPO certification typically outweighs the costs of implementation. Producers operating under this label can generally realize a 1 to 4% premium compared to those with non-certified product; however, implementation costs continue to present a barrier to entry for small holders. This is significant in Indonesia, where nearly 40% of growers are small holders; in other countries, the percentage is as high as 94%.

The three levels of RSPO certification, from lowest to highest are: mass balance (RSPO and non-RSPO oil can be mixed); segregation (RSPO-certified sources only); and identity preserved (end user product is uniquely identifiable to a single mill). Some growers have adopted an RSPO NEXT level of assurance that involves independent third party and accredited on-the-ground verification using standardized methods. However, even the highest level of RSPO certification is limited by currently available commercial tracking technologies and method.

Gaps in assurance can include the following:
  A cycle of 5-year re-certification with an annual audit is far below current tracking and auditing capability, yielding a static process.
  Document-based transactions and records are not wholly secure from fraud and abuse.
  Harvest from illegal areas is not necessarily detected because the RSPO process cannot trace fresh fruit bunches (FFBs) to the harvest site.
  Small holder growers are largely excluded due to implementation cost.

Certification programs rely on accurate information to establish and maintain credibility. As more advanced technologies become available, criteria and methods may need to be revised to keep goals and objectives aligned with processor and consumer expectations.

Real-time source assurance, transparency, and traceability throughout the supply chain are achievable by combining leading-edge technologies with new but already established ones. At the center of next-level palm oil source assurance is Applicant's on-product DNA barcode technology. The system provides the ability to create unique DNA barcodes onsite, apply them onto a product at the harvest or processing site, and verify source information within minutes using a simple on-site test. When integrated with satellite technology solutions to track land use and blockchain technology solutions to record a variety of tracking data in a secure digital ledger, an irrefutable audit trail is created from the harvest location to the mill. Adding unique DNA barcodes at other nodes in the supply chain extends the traceability solution—and thereby brand protection.

The four interlocking elements that create a verifiable and unbreakable audit trail are:
  Geo-location and time stamping—The location and time of harvest are digitally associated with the unique DNA barcode that is applied to product at the harvest site.
  Satellite imaging—Satellite images of the geo-located harvest site are monitored in near real-time to ensure that the harvest location is within a certified sourcing region and/or not in newly deforested areas.
  Unique on-product DNA barcodes—Unique DNA barcodes can be dispensed at the mill and distributed to harvesting crews. DNA barcodes applied at the harvest site at the plantation-level directly link to geolocation and time stamp data that is uploaded at the site via mobile phone. Products can be sampled and tested at the mill by quality assurance staff; results can be available within 15 minutes and automatically can enter the digital record. Unique DNA barcodes can be added at multiple strategic process nodes to track solid or liquid product. DNA barcodes are invisible and cannot be removed or adulterated because they are applied directly on the product. DNA barcodes have no effect on food flavor, shelf life, or odor. They are Generally Recognized As Safe (GRAS) by the United States Food and Drug Administration and are under review for use in the EU, where approval is expected in 2020.

Blockchain secured database—All data associated with each DNA barcode is secured using state-of-the art digital ledger technology.

First mile traceability is a defining problem of the palm oil supply chain. Indeed, a recent survey shows that most palm oil companies can't fully trace supplies, with only 19 or 83 companies able to trace from mill to plantation. Further, the boom in palm production has been correlated to damage to forests and wildlife. Existing traceability solutions are flawed in that they have limited scope, are vulnerable to fraud, and are impractical, costly, and exclude small parties. To date, stakeholders have failed to identify effective, practical, reliable, and cost effective solutions to these issues.

To address these ongoing problems, the present invention allows for: a) physical item-level tagging, which may include one or more geo-tags and time stamps; b) satellite monitoring of sourcing origins; c) digital data recording, secured via blockchain; and d) certification of suppliers and processes by third parties. For example, at the plantation site, a harvest crew may apply one or more unique DNA barcodes (taggants) to a product, such as palm fruit. The application can be achieved, for example, via an injector or sprayer linked to a smartphone. Each DNA barcode (taggant) application may create a data event that is recorded, timestamped, and notarized in a blockchain. By way of example, at the mill site, a quality assurance manager may conduct a detection test of a product, such as the tagged palm fruit, to confirm positive identification of DNA barcodes (taggants). The detection test results can be recorded, timestamped, and notarized in a blockchain and verified against other critical tracking data. This process can allow for highly accurate detection during first mile transit from the plantation to the mill.

This new leading-edge technology-enabled model for source assurance and brand protection has the ability to provide source assurance and brand protection, via unparalleled traceability for palm oil industry stakeholders all along the supply chain. As outlined herein, key elements particular to palm oil have already been proven in field testing and laboratory validation studies. The Applicant has also provided similar traceability solutions to growers and producers in other agricultural sectors, unrelated to palm oil. Working with various partners, this system has the potential to be comprehensive and scalable, and can accommodate global supply chains using Internet of Things (IoT) capability, as illustrated and in the exemplary processes and methods described herein.

The "next level" is the path forward. Efficient, versatile, and ubiquitous, palm oil has become an established staple in the supply chains of many major global brands. This tremendous success has come at a cost to the environment that includes an outsized carbon footprint due to rapid deforestation coupled with slash and burn clearing methods. The call for sustainably and ethically sourced palm oil is rapidly getting louder, particularly with the effects of climate change occurring more frequently than scientists predicted just a few years ago.

The palm oil industry has responded with an evolving RSPO certification process that has brought a broad spectrum of sustainability issues to the table. Gaps remain, and some of them can be addressed by pairing leading-edge technology with already established tools. The ability to dispense unique DNA barcodes onsite and an automated sampling system locks in source assurance. Management of records through blockchain technology locks in trust. These, together with geo-location and satellite imagery create a next-level system. Unique DNA barcodes can also be applied to any palm oil product at any strategic node to provide both traceability and brand protection by detecting dilution or substitution. Field and laboratory tests have validated this model, and work continues to refine its application.

The larger vision for a more sustainable future includes support at every level:

RSPO and certifying organizations—Partner with technology innovators, and modernize sustainability criteria, taking into account current climate change agreements and NGO partnerships.

Governments—Enforce policies, agreements and treaties, and limit new plantation permitting to areas with low carbon impact.

Growers and producers—Implement traceability technology, and enable inclusion of small holder growers into certification process.

Manufacturers—Implement traceability technology and require upstream growers and producers to do the same.

Consumers—Support brands committed to sustainable sourcing.

Application of DNA Taggants to Products

While a purchaser of a product, such as an agricultural product (e.g. palm fruit) might wish to deal with smaller vendors, perhaps even local growers, purchasers also wish to ensure that their supplier chains both produce quality fruit and are environmentally sustainable. Individual producers may produce small quantities, making verification of the origins of each difficult or inefficient. For example, individual producers (e.g., farmers) may leave small piles of fruit to be loaded onto a truck that may pick up product from tens of producers. Without tagging, tracing a particular fruit to a particular producer is impossible, making it impossible to grade individual producers. It also allows the addition of fruit from unapproved producers, making it difficult to ensure that the only fruit used is from producers who comply with sustainable or other standards.

To address the above-described problems, the piles of fruit or other product may be sprayed or otherwise marked with DNA taggants prior to collection or loading onto a truck. Each lot from each producer may receive a different DNA taggant set corresponding to a different tag string, associating individual lots with individual producers, or even identifying individual lots produced by the same producer. The DNA taggant may be applied directly to food and agricultural materials. The DNA taggant set may be mixed into a liquid carrier, allowing the DNA taggant set to be applied with an inexpensive spray bottle. The taggant may also be injected directly into an agricultural product, such as into the bunch stem or fruit or applied with a dropper.

The taggants may be combined with a colorant to ensure uniform coverage of the product or to allow visual confirmation that the product was tagged. In some embodiments in which a product, such as, a fruit, pods, or leaves is attached to a branch or stem that will not be used in the primary product, the taggant may be sprayed on or otherwise applied to the stem. The smaller lots may be collected together (e.g., loaded on the same truck) and transported to a central collection and processing facility. At the processing facility, inspectors may grade or sort the agricultural product or fruit. For example, inspectors may place a sample, such as one fruit or a small piece of product into a bin, cup, or other receptacle, which indicates acceptable or unacceptable. If a branch or stem were tagged, the branch or stem may be placed into the bin, cup, or other receptacle. The receptacle may be sealed and transported to a processing lab for analysis of the DNA taggant set to determine a tag string that indicates the producer of the product. Producers may then be given feedback on whether their product is acceptable. In another embodiment, there may be more grades than acceptable and unacceptable (e.g., unacceptable, poor, good, excellent, or grading on a scale). Multiple grades would allow more fine-grained feedback to the producers. Producers with consistently high quality product may be rewarded. Those with consistently low quality or unacceptable product may be asked to improve.

More generally, a DNA taggant set may be applied to a small lot of product by spraying the DNA taggant set on the product, immersing the product, or otherwise applying the DNA taggant set to the product with an application device. The DNA taggant may also be applied to a stem, branch, root, husk, or other discarded attachment of the product rather than to the processed part of the product. After the DNA taggant set is applied to the small lot of product, the small lot of product may be combined with other small lots to form a larger aggregated batch of product, large enough to be transported and processed efficiently. During processing, individual units or portions of the product may be sampled or inspected for grading. The grading may be binary (e.g., acceptable or unacceptable) or may be more fine grained (e.g., unacceptable, poor, good, excellent, or grading on a scale). The grading may be done by attaching a grading label to a sample (e.g., adhesively or mechanically), by placing the sample in a labelled receptacle, or by marking the sample (e.g., with ink or paint). In an embodiment in which the taggant is applied to a stem or other attachment to the product, the attachment may be labeled, placed in the receptacle, or marked. The graded sample or attachment may be analyzed to determine the DNA taggant set, which in turn correlates to the tag string, which in turn correlates to the producer or lot, allowing the grade label from the label, receptacle, or mark to be associated with the producer or lot.

A conventional sprayer might be used as an application device, for spraying DNA taggants that are in a fluid suspension. Each grower might operate their own application device. That application device might be configured to vary the DNA taggant combination that is used over time, thus generating a unique DNA taggant combination code for each lot. The grower preferably ensures that the sprayer or other application device is thoroughly cleaned between applications to prevent cross contamination of one set of DNA taggants with another set. In another embodiment, the same DNA taggant combination may be used for a larger lot or to identify producers, and the DNA taggant combination may be changed infrequently (e.g., a few times a day). The taggant combination may be distributed from a premixed taggant combination or may be mixed in a sprayer's manifold to produce the required taggant combination.

In one embodiment, a quality assurance representative from a processing facility, such as a mill employee, may provide a particular DNA taggant having a specified DNA bar code to a harvester in an application device, such as, for example, a sprayer. The quantity of the taggant may be measured to match the expected amount of agricultural product or fruit the harvester will harvest. The mill may also provide an application device (e.g., a sprayer or injector) or combination of devices to apply the taggant. The application device may have an internet or satellite connection that records the location and time of application of the taggant. It may additionally or alternatively have a local storage device, such as a hard drive. It may log the location and time locally or may send the location and time to a server to record the location and time. In one embodiment, the application device may be a sprayer having a cellular data connection and GPS unit, allowing the sprayer to log its GPS coordinates whenever the sprayer is triggered.

In another embodiment, an applicator, such as, for example, a sprayer, may have a Bluetooth connection to a cellular phone and may prevent application of taggant without confirming the device's location or connectivity. The device may either access or have stored within device geographic coordinates within which it is expected to operate and may shutdown when outside of those coordinates, preventing the applicator, such as, for example, the sprayer from tagging the agricultural product or fruit outside of the plantation it is meant for. The applicator, such as, for example, the sprayer might also record GPS coordinates, timestamps, and other data about the application of the taggant. When a lot is returned to the mill then all the information about when and where each bunch was tagged is validated before the lot is accepted. For example, if the applicator, such as, for example, the sprayer was actuated more than would be expected given the harvest size, this overuse of taggant may trigger an error or flag that causes further investigation.

Recording a time at which the application device applies the DNA taggant set to the first batch of the material and verifying that the time is within an expected time range might be performed at a quality control point to validate product.

The sprayer or other application device might only dispense enough taggant in each spray for labeling a certain size lot, allowing the processor to perform a rough mass balance by counting the number of lots received. The applicator, such as, for example, the sprayer might only work within certain times and may have an expected range of actuations. Exceeding the time or number of actuations may cause the applicator, such as, for example, the sprayer to cause an error message or stop working. The processor receiving the lots might perform a mass balance by counting the number of lots received and verifying the number of lots that were labeled with the application device. The time stamps, locations, and number of the applications of the taggant, plus the verification of the taggant at the processing facility, allow the processor to verify that the lots received at the processor facility is agricultural product or fruit that was harvested when and where the harvester claims it was harvested. The number of lots received allows the processor to perform a mass balance by comparing the number of lots received to the number of lots that had taggant applied, according to the logs from the application device. The amount of taggant issued to the harvesting crew may be sufficient only for labeling the expected amount to be harvested, limiting the possibility that agricultural product or fruit from other plantations is transported to the approved plantation and added to the agricultural product or fruit lots that are from the approved plantation. Additionally, a number of actuations of the applicator, such as, for example, the sprayer may be expected given a certain harvest size, calculated from field size, and an actual number of actuations above an expected number of actuations may cause an error condition.

In a particular embodiment, the dispenser is coupled to a network to provide usage data and the dispenser applies the taggant consistently such that the amount of taggant dispensed per unit (per lot, per plant, per bunch, per unit of mass, per unit of volume, etc.) of product is predetermined, at least within a narrow range. The operator of the dispenser might be provided with application instructions, including an explanation that credit will only be given to units that are marked and that the dispenser's material is constrained to only last through a predetermined number of applications. Knowing that, the operator would be careful not to overapply the taggant material (or else the operator might run out of taggant material and still have units to get credit for) or underapply the taggant material (or else credit might be reduced downstream in the supply chain for lack of sufficient marking). The mill may have information about the number of acres the harvester will cover, and the number of plants for a specific crop may be reasonably fixed. If a harvesting crew is assigned to a particular parcel, the number of expected fresh fruit bunches may be estimated fairly accurately. In the case of palm fruit, the number of plants per acre is reasonably fixed, and the yield of the palms is fairly constant, with harvesting occurring on a predictable schedule. When the harvester goes to a particular parcel, the expected harvest is capable of estimation.

The supply chain may have points at which mass of the product is determined and the source identified, so that a mass balance can be performed. If the dispenser has enough for N bunches and once a lot is delivered and the packing list is read, the two are reconciled (the actual lot and the amount the dispenser says is marked).

DNA taggants correspond to encoded information that can be applied to objects, including food items, in a manner that allows for later reading of this encoded information from the objects. In a specific embodiment, the DNA taggants are unique, each taggant represents a bit position and the pattern of presence or absence of one of the DNA taggants corresponds to a bit value of 1 or 0 and the pattern of DNA taggants that are present or absent forms a binary number representing the encoded information. In another embodiment, the presence of a first DNA taggant is used to signal a value of "1" of the encoded information and the presence of a second DNA taggant is used to signal a value of "0" of the encoded information. The apparatus that adds the DNA taggants to the objects can be configured such that the encoded information can change from object to object and not cross-contaminate objects with DNA taggants that are for one object but not another.

In a specific example, there is a set of 32 DNA taggants to work with and so there are $2^{32}$ possible combinations of DNA taggants that can be applied to an object, thus encoding the object with a 32-bit value corresponding to a specific "tag string" that might be represented by a sequence of 32 binary values each having a bit location in the tag string. It should be understood that other numbers are also possible and in the general case, a tag string might be represented as an indexed array of values, each having an index or position in the tag string, where the values might be binary values.

For example, it might be that 28 bits (and 28 DNA taggants) would be sufficient for a particular application. For example, if there are 128 producers of apples, each having 8 facilities, and they group their apples by lot such that they output 256 lots per year, one per day, over the course of 16 years, the manufacturer, facility, lot, and year can be encoded in a 7+3+8+4=22 bit tag string and so 22 bits and 22 DNA taggants are sufficient and that leaves room for checksum bits/taggants to be added. In this simplified example, the number of possible values for each of the variables is a power of two, but that is not required and other values can be used. Conventional mapping of values to tag strings can be done.

As used herein, a DNA taggant is a material that includes an oligonucleotide and possibly other material. In a specific example, each DNA taggant comprises a static part and an identifier part, wherein all of the DNA taggants have the same static part and thus it can be used to differentiate between the set of DNA taggants in use and other DNA that might be present in a sample. Preferably, the presence of a DNA taggant can be done even when there are very low concentrations of the DNA taggant in or on the object. Thus, where there is a dispersant expected to be found in the sample, the sample and/or the dispersant thereon is sampled, detected, error-corrected as needed, etc. to determine the tag string that was applied to the object.

A tag string has an associated DNA taggant set (sometimes called a "DNA bar code"), which is a selection of particular DNA taggants used, or to be used, on an object to "label" that object with the tag string. The object might be an item being sold, bulk material, packaging, or other physical object or item where labeling according to the tag string is useful. In particular, where a printed label is not workable or viable, applying the tag string could be done instead. For illustration purposes, consider the case where the tag string comprises binary values each having a bit position in the string, such as "01101001 10101001 10100111 10010101" which has a "0" in the first bit position, "1" in the second and third bit positions, and "1" in the 32nd bit position. The bits may ordered from most to least significant or vice versa. A specific DNA taggant is associated with each bit position of the tag string and labeling an object might comprise determining which bit positions of the tag string are "1," determining which DNA taggants go with those bit positions, and applying those DNA taggants (referred to herein as a "taggant set") to the object, and not applying the DNA taggants that go with the bit positions of the tag string that have "0" values. Alternatively, pairs of DNA taggants might be used, wherein the presence of one taggant indicates a "1" in a position and the presence of the other indicates a "0" in that position. Though this approach uses twice as many taggants for the same number of bits of information, it provides error checking. Other approaches used error checking codes are possible.

The tag string could represent different information. For example, in a particular industry or application, some of the bit positions might correspond to the company name, others to a serial number, others to a production date or location, etc. By later sampling the object on which the taggant set was applied, a tag detecting system can decode the taggant set and from there determine the tag string that was applied to the object.

In some embodiments, all or part of the tag string is an index value that points to a record in an external database that provides data about that particular record. In those embodiments, the tag string assigned to an object might be entirely arbitrary and an external database of object information would be used to get data about the object rather than decoding any data about the object from the bit pattern itself.

In an example distribution system, there are lots and each lot has applied to it a specific tag string and a first lot receives a first taggant set corresponding to a first tag string and then a second lot receives a second taggant set corresponding to a second tag string different than the first lot. The first lot might be multiple items, such as a plurality of melons, or the first lot might be a single item, such as a bag of coffee beans. In the case of a bag, the distribution system might be integrated in with an automated bag filling line. In such a line, a new bag is positioned in the system and is clamped to the filling line chute to receive product. Perhaps before the first bag is in place, the distribution system initially dispenses plain carrier (no taggants) in the "dead volume" (the volume of the piping beyond actuating valves). Then when the empty bag is in place, or after the bag is filled, but before it is declamped and stitched closed, the distribution system actuates certain valves of the distribution system to push out the plain carrier and then push out specific taggants based on that bag's designated tag string. It may be that delivery is timed so that the plain carrier residing in the dead volume is delivered during clamping to the bottom of the empty bag and the taggants are delivered as the product is filling the bag. The taggant valves may be de-energized before the bag is full while the plain carrier valve remains energized, so that at the completion of the bag filing cycle, the dead volume has been filled by plain carrier, at which point the plain carrier valve is de-energized. The cycle repeats with a new taggant combination for the second bag and so on with the plain carrier effectively flushing the lines so that only the desired taggants appear for a given lot.

Instead of a spray, the carrier/taggants might be applied by immersion.

The carrier can be liquid or solid or in between, as might be the taggants. The taggants might be naked DNA or DNA included in a matrix, such as a carnauba wax coating, as is often used for various types of fresh fruit, or if the carrier is a volatile liquid such as ethanol, water, etc., the taggant remains in direct contact with the product. Studies have shown that its stability is limited and generally shorter than the product shelf life relative to being included in some persistent matrix.

In a solid form such as a powder, the taggant might have been previously encapsulated in a solid carrier (such as maltodextrin, gelatin, etc.), which can provide superior stability that is usually in excess of one or two years. The solid form is a convenient form for application of taggants to dry and granular products such as flour, sugar, etc. Taggants encapsulated in solid matrixes can also be used in processed foods and liquids (e.g., juices, oils, etc.) preferably encapsulated in a solid matrix that does not dissolve in the product, as that would release the DNA of the taggant and may limit its stability.

For commodities such as fertilizers, beans, grains, etc., application of taggants in solid form (encapsulated) might be preferred due to stability considerations. However, for high speed processes, as when, for example, a taggant must be uniformly applied to product during the bag filling process (which might be a 2-4 second cycle), liquid carriers might be preferred as powder can be very difficult to manage at those speeds and prone to cross contamination. A cost effective method to apply a taggant in solid form is as very fine powder, which increases the number of taggant particles per volume of product. This increases the probability that the taggant will be recovered from a small sample of product when the product is tested for the presence of the taggants. However, when fine particles are used, they may remain airborne for minutes or even hours, possibly migrating to lots where they were not intended to be applied, which would cause identification errors when taggant reading is done on a sample of the product. Loose particles also might cause cross-lot contamination at the point of testing as the product is taken out of a bag. In these situations, application of the taggants in a liquid form would simplify the application process but might result in diminished stability.

In an improved application process, a hybrid method is used that combines the ease of the liquid application with the stability of the solid carriers. In this approach, the taggant is encapsulated in powder granules that are suspended in a liquid in which the granules do not dissolve. Examples of encapsulating carriers include gelatins, agarose gel, carrageenan powder, etc. and the liquid carrier might be ethanol. Another example is ethyl cellulose powder as the encapsulating carrier and water as the liquid carrier. The distribution system can then spray a product or immerse the product, thus improving uniform application and reducing the potential for loose powder and resulting cross contamination. The amount of liquid carrier required is usually very small (in one example, less than 50 mL per 50 kg bag). The liquid carrier either evaporates or is absorbed by the product leaving the taggant as an encapsulated powder in the sealed bag.

In addition, use of gels promotes adhesion of the powders to the product, reducing the risk of contamination due to loose powder when the bag is opened. Other adhesives may be added to the liquid to promote adhesion. For example, applying ethyl cellulose powder suspended in a 0.5% agar-agar solution will create a film containing ethyl cellulose DNA tagged powder on the surface of the product.

A dispensing system might include tanks or vessels that contain one of the DNA taggants (or taggants in encapsulating carriers) in suspension, powder, or other forms such as emulsions, liposomes in liquid, or coacervations (a type of electrostatically-driven liquid-liquid phase separation, such as spherical aggregates of colloidal droplets held together by hydrophobic force measuring from 1 to 100 micrometers across or some other diameter, while their soluble precursors are typically on the order of less than 200 nm or some other distance). A computer control system might control the dispensing of specific patterns of the DNA taggants. The taggant vessels have a finite volume and so DNA taggant gets consumed. By careful selection of which patterns are used, the consumption can be controlled so that the taggant vessels do not need to be filled at inconvenient times.

The dispensing system might be required to deliver distinct taggant sets (thus marking distinct objects or lots with different tag strings) at very high speed, as many as 20-25 per minute or more. In an implementation, a computer processor determines what tag string is to be applied and then sends electrical signals and commands to various modules, ultimately resulting in the desired taggant set being added or applied to the object being marked. It may be that each object marked gets a different taggant set, so the dispensing system would carefully control the distribution of taggants so that the taggants of the taggant set applied to a current object do not get used during application of a next object (unless those are taggants that are part of the taggant set for both the current object and the next object).

Exemplary System

According to one embodiment, the techniques described herein are implemented by one or generalized computing systems programmed to perform the techniques pursuant to program instructions in firmware, memory, other storage, or a combination. Special-purpose computing devices may be used, such as desktop computer systems, portable computer systems, handheld devices, networking devices or any other device that incorporates hard-wired and/or program logic to implement the techniques.

FIG. 1 is a flowchart illustrating a method of tagging a product to indicate the producer of the product. As shown there, the process begins with a mill quality assurance representative estimating the required taggant set (step 101) for the harvest. This may be based on the size of the parcel the harvester will cover, the density of the plants in the parcel, and the expected yield per plant. The mill may fill a applicator, such as, for example, a sprayer with the estimated amount of taggant and issue the applicator, e.g. sprayer (step 102) to a harvest crew. As the harvest crew collects the fresh fruit bunches, the crew may apply the taggant set to a product from a producer (step 103). As explained above, a taggant set is a collection or aggregation of independent DNA taggants used to tag a product such as a food product or other item. The taggant set might be aggregated from individual vials or containers that supply specific individual DNA taggants and the aggregate of the set does not require that the individual DNA taggants be joined. As a result, the taggant set can be created with much simpler equipment, such as using simple conduits from tanks as opposed to DNA-joining equipment.

Following the taggant application, the product might be aggregated with other product of a similar type (step 104). For example, the products might be palm oil fruit, bananas, or other agricultural product and the aggregate might be those agricultural products from different farms, where each farm has tagged their respective product with a taggant set that is designated for that farm. At a processing center or other location, the product might be sampled (step 105) and graded. Once sampled/graded, a processor or inspector might determine the taggant set (step 106) of a particular product, perhaps by obtaining a set of sample DNA taggants detected from the product. The processor or inspector might then use a computer system or records system to associate and determine the farmer or producer that was designated that taggant set (step 107). For example, where the DNA taggant set comprises a taggant material including at least N unique pieces of DNA, representing N digits of a bar code that identifies the farmer/producer of the product, the process might involve detecting detected pieces of DNA applied to the product, deriving a derived bar code from the detected pieces of DNA, and comparing the derived bar code to a predetermined bar code that identifies the farmer/producer of the product.

Using that information, the processor or inspector can associate a product grade with a farmer or producer (step 108). This processing and association can occur at various places in the supply chain, as the taggant set might be expected to persist as the product travels and even after certain processing steps.

Figure 2:
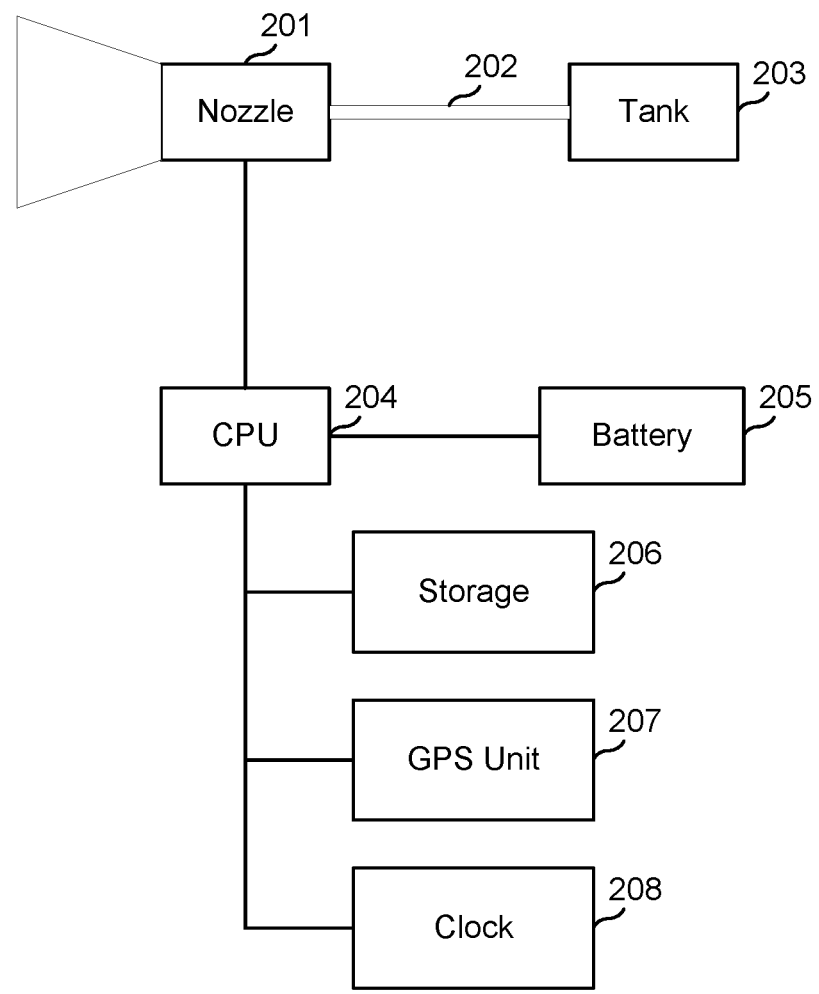
FIG. 2 is a block diagram of an exemplary application device.

FIG. 2 shows a block diagram of an exemplary application device, in this case a sprayer having a nozzle 201 connected to a tank 203 by a tube (such as a pipe or plastic tubing) 202. The nozzle 201 is electrically connected to CPU 204, allowing the CPU to record actuations of the nozzle in storage 206. The CPU may be connected to a GPS unit 207, allowing the CPU to also record the location of actuation in storage 206. The CPU may also be connected to a clock 208 to allow the CPU to record the date and time of actuation. A battery 205 may be electrically connected to the CPU 204 to provide power to the CPU.

Figure 3:
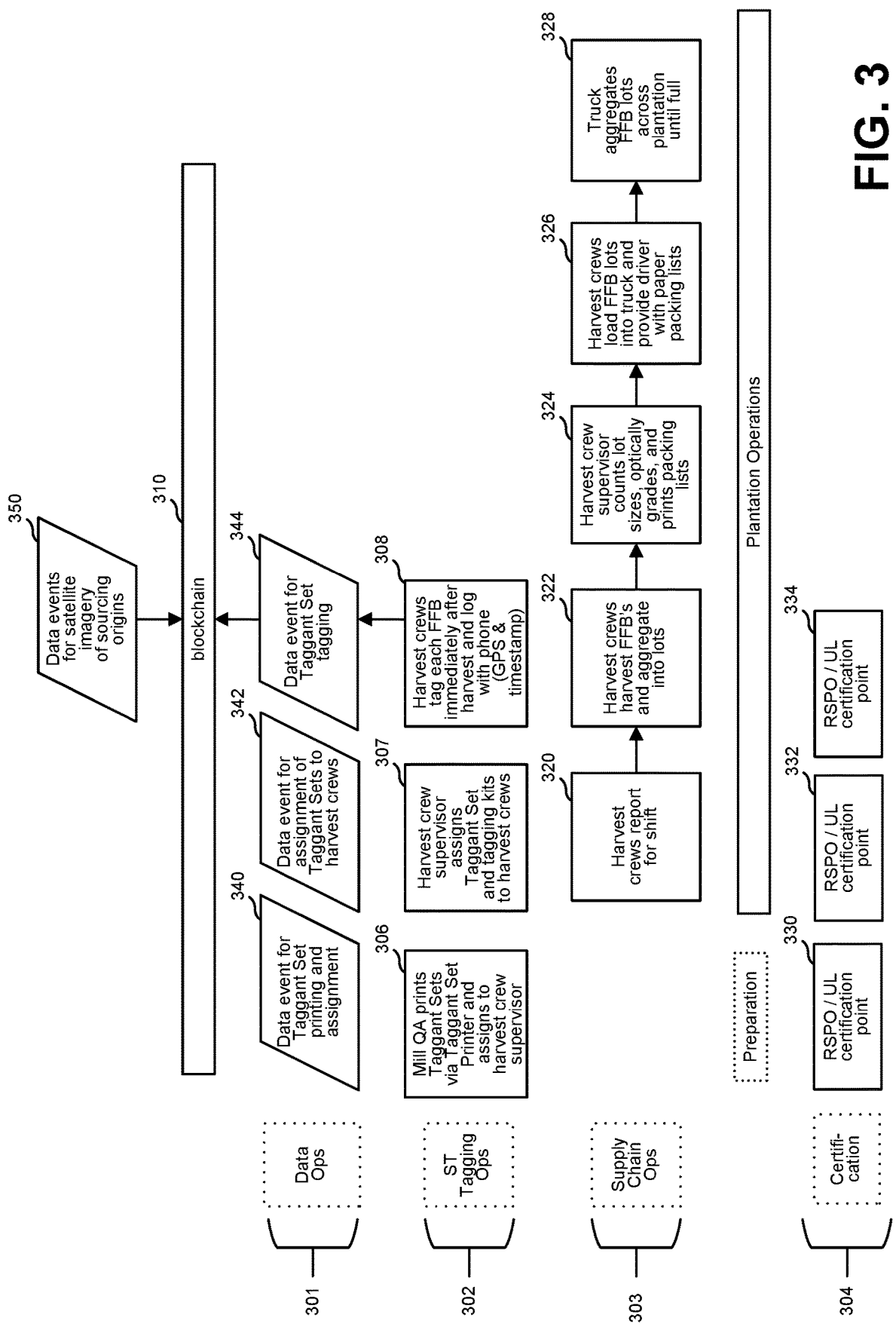
FIG. 3 is a flowchart illustrating a method of tagging in plantation operations to indicate the producer of the product.
Figure 4:
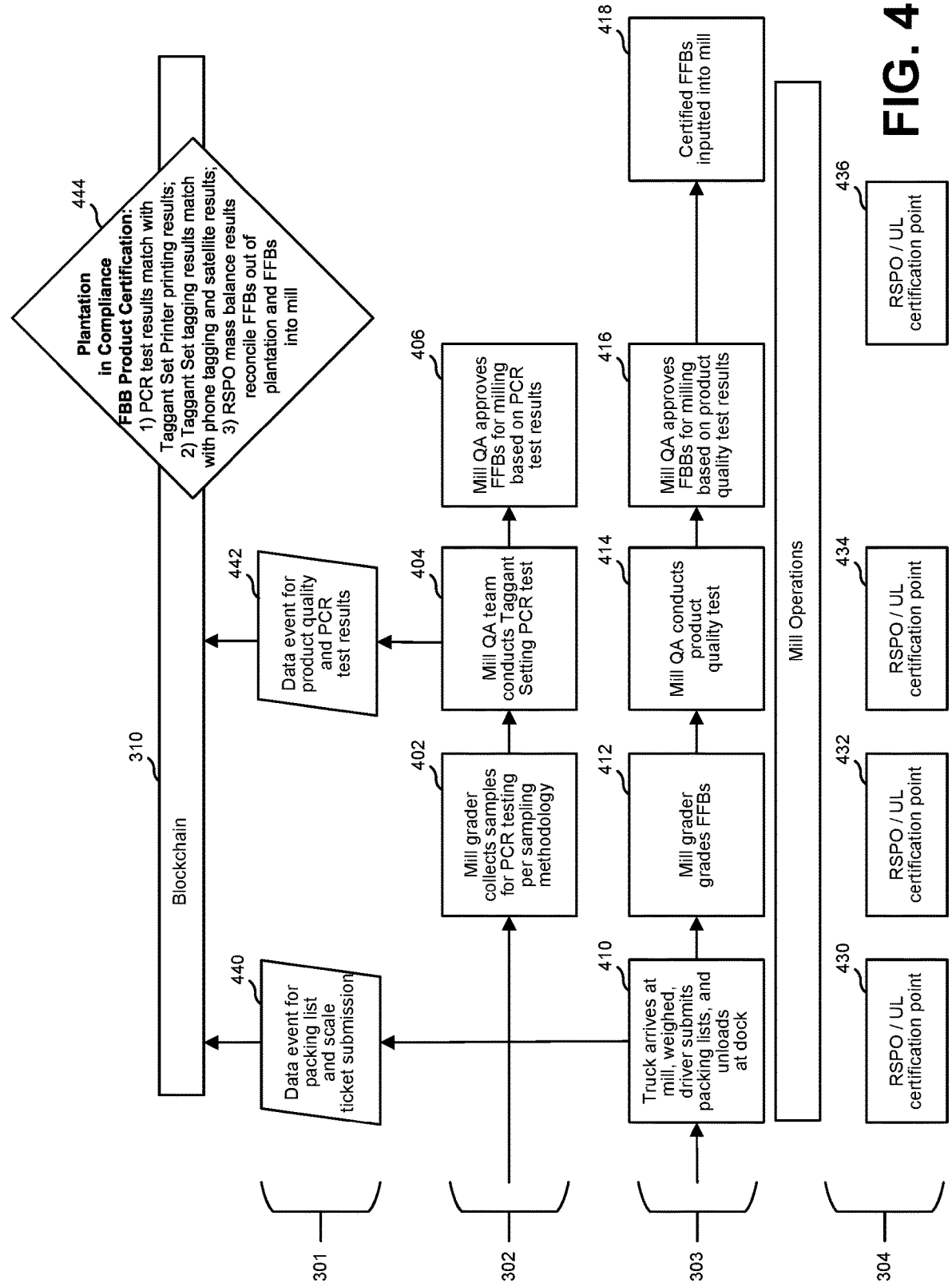
FIG. 4 is a flowchart illustrating a method of tagging in the reception stage of mill operations to indicate the producer of the product.
Figure 5:
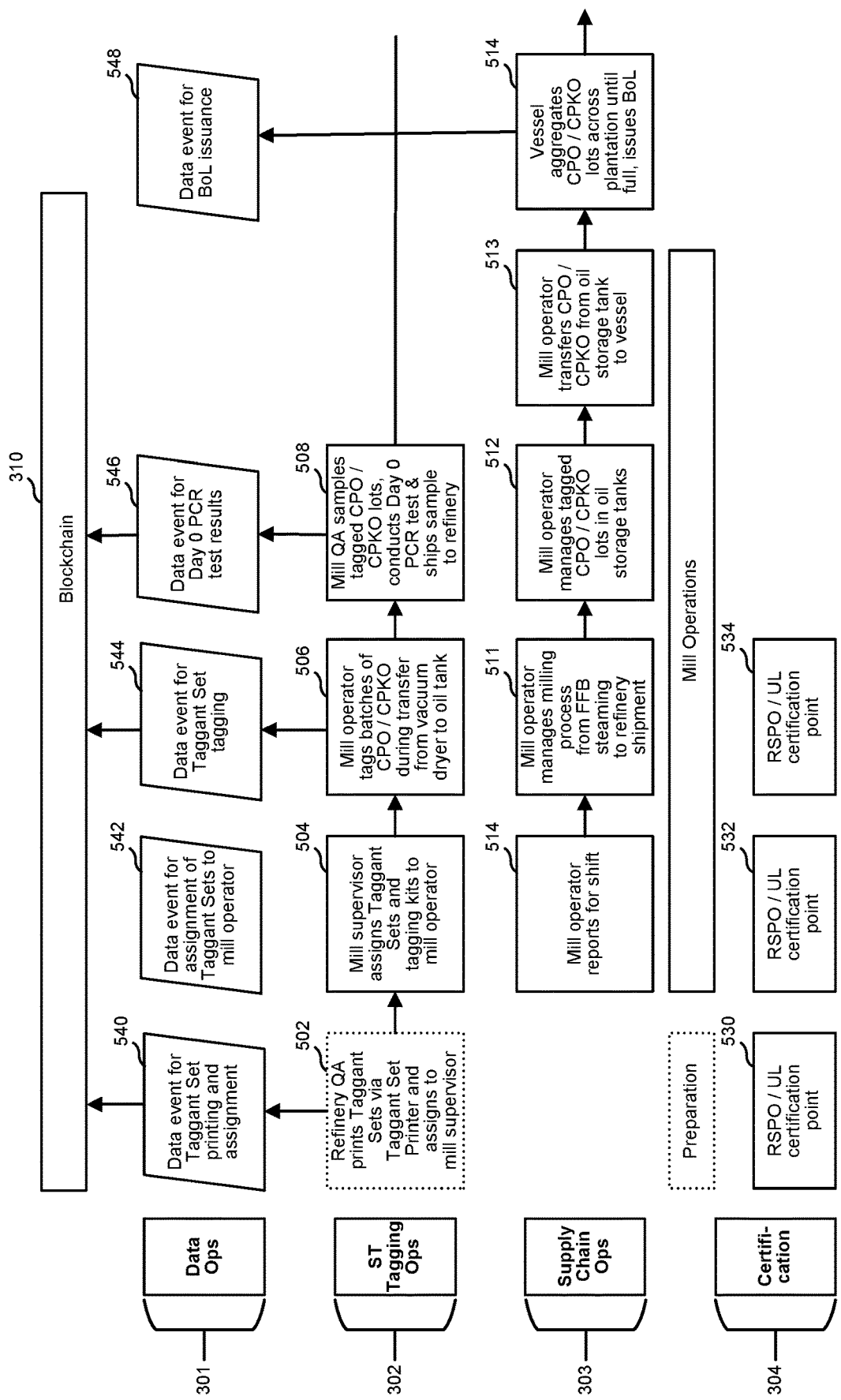
FIG. 5 is a flowchart illustrating a method of tagging in the milling portion of mill operations to indicate the producer of the product.

FIGS. 3-6 show further details of this process as an exemplary fruit, palm fruit, is harvested at a plantation (FIG. 3), received at a mill (FIG. 4), processed at the mill (FIG. 5), and processed at a refinery (FIG. 5). Though the process is shown with respect to palm fruit, it may apply equally to other fruits or agricultural products.

The four rows in FIG. 3 show different elements of harvesting operations: a row for data operations (row 301), a row for tagging operations (row 302), a row for supply chain operations (row 303), and a row for certification operations (row 304). In the first column in the tagging operations row 302, at step 306, the mill quality assurance representative creates the taggants (referred to there as "SafeTracers" taggants) via a process similar to bubble jet printing. In some embodiments, this is done using a Mini-DART™ system provided by SafeTraces, Inc. The Mini-DART™ system may apply one or more taggants directly on a product, such as an agricultural product, fresh produce, or a dry or liquid commodity, at item-level, enabling rapid tracing to the product source. The taggants contain a unique tag assigned to the harvest crews and issued to harvest crew supervisors. This allows the mill that will receive the agricultural product or fruit to verify the origin of the agricultural product or fruit and create a chain of trust from the mill back to the plantation. The unique tag assigned to the harvest crew may be entered into a blockchain 310 or other database (step 340). The issuing of the taggant may be part of a certification body or point, such as, for the example of palm oil, a roundtable on sustainable palm oil (RSPO) certification point, labeled in row 304, in certification step 330.

In the second column of FIG. 3, the harvest crew supervisor issues the taggants to harvest crews (step 307). This may include issuing both the taggants and tagging kits for applying (e.g., spraying or mixing with) the taggant to the fruit. The taggants and kits may be issued when the harvest crews report for their shifts (step 320). This may also be a certification body or point, such as, for the example of palm oil, an RSPO certification point, shown in row 304, certification step 332. This information may also be stored in the blockchain 310 or other database, shown as step 342. In the third column, the harvest crew harvests the fruit and may, immediately after harvesting the fruit, tag the fruit with the taggant and log the harvest (step 308). The harvest crew may also label the fruit with conventional labels, such as by applying labels to containers or bundles of the fruit or by applying labels directly to the fruit. The taggant logging may be done with a GPS and internet enabled device such as a smart phone, and this information may be uploaded immediately to the blockchain 310, shown in step 344, or may be stored and uploaded later. A satellite system may also be used, for example a satellite phone or other geo-locating system, which allows proof of a devices location to be provided. This information may be combined with satellite or other imagery data 350 to provide a further check on the accuracy of the data. The data may be entered into the blockchain 310 or other database. The crews may tag the fruit before, during, or after aggregating the fresh fruit bunches (FFBs) into lots (step 322). In one embodiment, smaller bunches of fruit may be tagged prior to consolidation into lots to facilitate applying taggant to each bunch. The tagging step may also be a certification body or point, such as, for the example of palm oil, an RSPO certification point (certification step 334). After the tagged fruit is aggregated, the harvest crew supervisor may count the lot sizes, optically grade the fruit, and print packing lists (step 324). The harvest crews may then load the fruit lots into a truck and provide the driver with the paper packing lists (step 326). The truck may aggregate fresh fruit bunches across multiple crews and even across plantations until the truck is full (step 328). The individual lots will be labelled both with conventional labels and taggants.

FIG. 4 illustrates the process when the fresh fruit bundles arrive at a mill. As before, the four row correspond, from top to bottom, to data operations 301, tagging operations 302, supply chain operations 303, and certification operations 304. In column 1, step 410, the truck full of the fresh fruit bundles arrives at the mill and is weighed. The driver submits the packing lists and the truck is unloaded at a loading dock. The packing list and scale ticket may be logged in the block chain, as shown at step 440. This may be a certification body or point, such as, for the example of palm oil, an RSPO certification point, shown by certification point 430. After unloading, at step 412, the mill grades the fresh fruit bundles. Before, during, or after grading, the mill may collect samples from the fresh fruit bundles for testing via barcode detection methods/instrumentation, such as, for example, via polymerase chain reaction (PCR), at step 402. This may be done per some sampling methodology (e.g., check every tenth bundle, check random bundles, check every bundle, etc.). This step may also be a certification body or point, such as, for the example of palm oil, an RSPO certification point, shown by certification point 432. In the third column, mill quality assurance conducts product quality tests (step 414) and performs the barcode testing, such as, for example, PCR testing (step 404) on the taggants (referred to as "SafeTracers" taggants in the figure). The outcome of the barcode test, such as, for example, the PCR test is logged (step 442) in the blockchain 310 or database and may also be a certification body or point, such as, for the example of palm oil, an RSPO certification point 434. If the fruit passes the product quality tests (step 416) and the barcode tests, such as, for example, the PCR tests confirm the taggants match those expected based on the origin of the fruit (step 406), the certified fresh fruit bundles may enter mill processing at step 418. Completion of quality tests and PCR confirmation of origin may be a certification body or point, such as, for the example of palm oil, an RSPO certification point 436. The plantation that provided the fruit may be proven to be in compliance by the barcode test, such as, for example, the PCR test results that match the taggants. The taggants might be the DNA snippets applied by a MiniDART™ system. The data entered into the blockchain or database with the taggants may also represent a record of the phone tagging and satellite location results, verifying that the fresh fruit bundles were harvested in the geographic region of the correct plantation. The data 444 in the blockchain or other database provides a log of certification. The packing lists and weights of the truck can be used to record a mass balance of fruit entering the mill.

FIG. 5 illustrates operations at a mill once the fresh fruit bundles have been graded and verified via barcode testing, such as, for example, PCR testing of the taggants. The four rows correspond, from top to bottom, to data operations 301, tagging operations 302, supply chain operations 303, and certification operations 304. In the first column, at step 502, the refinery quality assurance representative prints taggants (referred to there as "SafeTracers" taggants), possibly using a MiniDART™ machine to create the taggants. This may be a certification body or point, such as, for the example of palm oil, an RSPO certification point 530. This time, the taggants are assigned to the mill by the refinery, creating a chain of trust from the refinery to the mill. Since the mill has a chain of trust to the plantation, possibly stored in blockchain 310, the refinery can trace the origins of its product back to specific plantations. The refinery quality assurance representative may print the taggants using a MiniDART™ or other taggant issuing machine and assign the taggants to the mill. This data event may be entered into the blockchain 310 or database at step 540.

In a continuously operating mill, in which the product leaves relatively soon after processing, taggant applied to the outgoing product may be linked to the lots or bunches that were received the same day, creating a link between the outgoing product and the plantations whose fruit was processed that day. Tagging the product as it exits the mill may be a certification requirement, such as, for the example of palm oil, an RSPO certification requirement 532. After the taggants are issued to the mill, the mill supervisor assigns the taggants and tagging kits to the mill operators at step 504. In this instance, the taggant kits may be applicators, e.g. sprayers, or may be droppers or bottles adapted to mix the taggant with a fluid.

The mill operators may receive the taggants and kits when they report for a shift (step 510) or when a new shipment of fruit is received. This may also be a data event 542, which may or may not be logged in the blockchain 310 or other database. As the mill operator manages milling processes such as steaming to refinery shipment (step 511), batches of crude palm oil (CPO) and crude palm kernel oil (CPKO) will be created. As the mill transfers the batches of CPO and CPKO from vacuum dryers to oil tanks (step 506), the batches may have the taggant mixed with them or otherwise applied to them, as well as conventional labelling of tanks. This event may be a data event 544 that is entered into the blockchain 310 or other database as well as a certification point, such as, for the example of palm oil, an RSPO certification point 534.

A mill QA representative may sample (step 508) the tagged CPO/CPKO lots and conduct initial (day 0) barcode tests, such as, for example, PCR tests, and then the lot may be shipped to a refinery, without being mixed with other lots. This information may be entered into the blockchain 310 or other database at data entry step 546. The mill may remove a sample and ship the sample to the refinery in a tamper-proof container. The refinery may then analyze the taggant, including the taggant concentration, in both the sample and the shipping tank, comparing the taggants and concentration. Lower taggant concentration in the shipping tank would indicate that the shipment had had unapproved liquid added to it or been adulterated in some way. In another embodiment, the mill operator may also manage (step 512) the tagged CPO/CPKO in oil storage tanks, for example if the mill maintains custody of the CPO/CPKO lots for a period of time before shipping to a refinery. In such an embodiment, the mill operator may transfer (step 513) CPO/CPKO from an oil storage tank to a larger oil storage vessel. The vessel may aggregate (step 514) CPO/CPKO lots across plantations until full, and the mill may issue a bill of lading (BoL) or packing list, that may be a data event (step 548) entered into the blockchain or other database.

The concentrations at application might not always be consistent and the taggants are subject to some degradation over time. If a sample is collected and shipped ahead of a lot and the sample taggant is subject to the same level of degradation as the lot itself, that degradation can be factored out.

Where the material tagged is a liquid, if two smaller portions of liquid are tagged differently and then combined, it may be that the mixed result will have DNA snippets from each of the taggants of the smaller portions. If the DNA snippet set used was the same in both small portions, but with different selections of DNA snippets to represent different bar codes being applied to each smaller portion, it may be that the barcoding is not recoverable from the mixed result, as the taggant of the mixed result would be a bitwise-OR of the bar codes of the two smaller portions. To avoid this ambiguity, different sets of snippets might be used for the two smaller portions, or the details of the mixing, such as, which small portions were used in the mix, might be recorded along with a new bar code that is applied to the mix and uses a set of DNA tags that is distinct from the sets used for the smaller portions. At that time, the components might be identified and validated prior to combining the lots and then a new taggant representing the resulting blend is tied to the IDs of the components.

Figure 6:
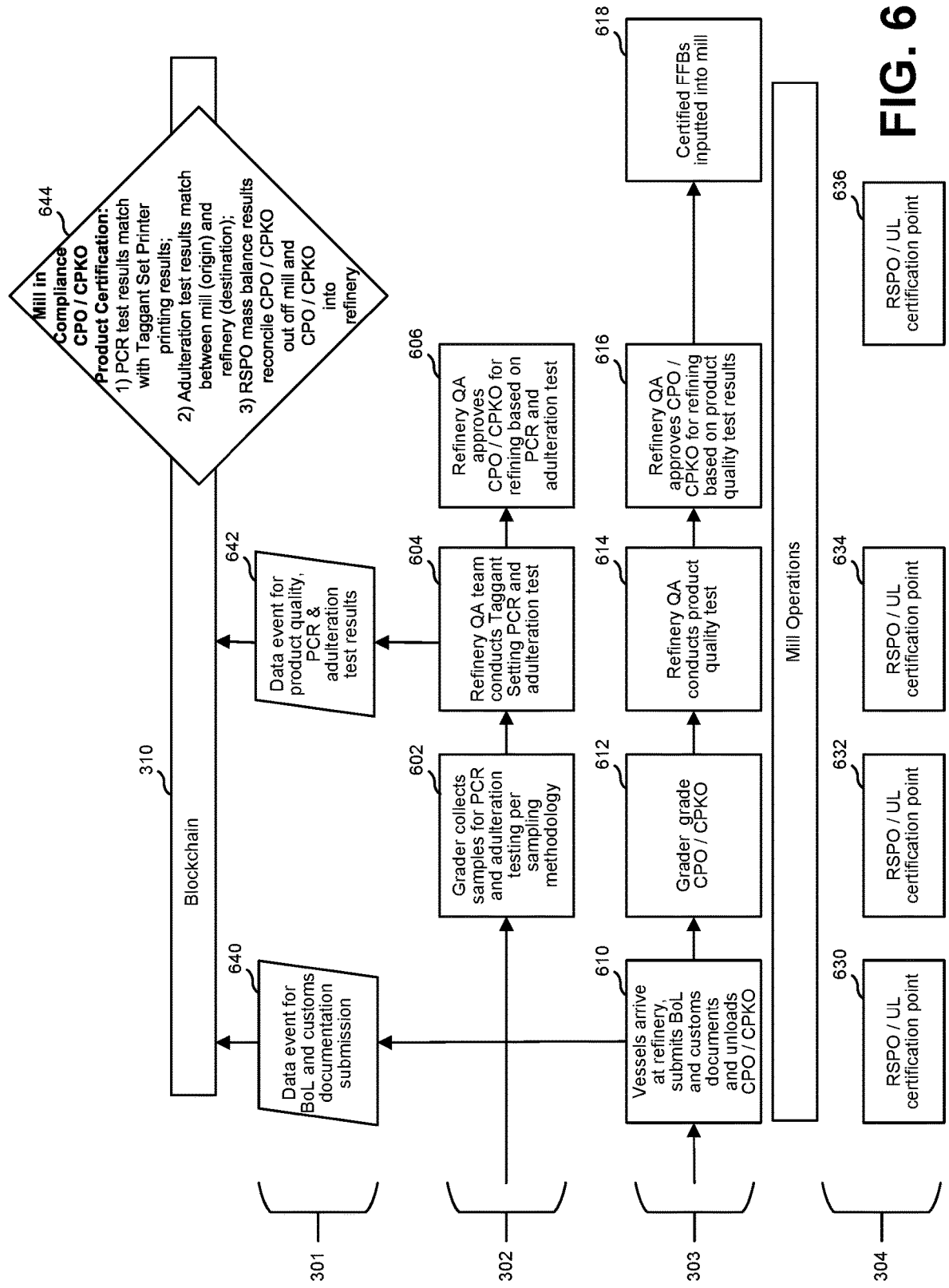
FIG. 6 is a flowchart illustrating a method of tagging in refinery operations to indicate the producer of the product.

FIG. 6 illustrates refinery operations. As before, the four rows correspond, from top to bottom, to data operations 301, tagging operations 302, supply chain operations 303, and certification operations 304. In an embodiment where the refinery receives a vessel (e.g., combining multiple lots) from the mill (step 610), the mill will also provide a packing list, and possible customs documents, to the refinery. This data may be entered in the blockchain or other database at step 640. The refinery will unload the CPO/CPKO, which may be certification step, such as, for the example of palm oil, an RSPO certification step 630. At step 612, a grader for the refinery will grade the CPO/CPKO, which may be a certification step, such as, for the example of palm oil, an RSPO certification step 632. At step 614, the refinery QA representative will conduct product quality tests, which may also be a certification step, such as, for the example of palm oil, an RSPO certification step 634. Once the refinery QA representative approves the CPO/CPKO based on product quality tests at step 616, the certified CPO/CPKO may be entered into the refinery for processing at step 618.

Continuing with FIG. 6, the second row 302 from the top shows an embodiment where the CPO/CPKO is transported to the refinery in a specific lot, without being mixed into a larger vessel. A grader for the refinery collects samples (step 602) to verify the taggants by barcode testing, such as, for example, by PCR testing and to check for adulteration (e.g., dilution with another product or non-certified CPO/CPKO) per a sampling methodology (e.g., drawing a sample per lot, or periodically sampling as the lot is moved from one tank to another). This may also be a certification point, such as, for the example of palm oil, an RSPO certification point 634. At step 604, the refinery QA representative may then conduct barcode testing, such as, for example, PCR testing and adulteration tests, entering the results (step 642) into the database or blockchain 310. This may also be a certification point, such as, for the example of palm oil, an RSPO certification point 634. Based on the barcode test, such as, for example, the PCR test, and adulteration tests, the CPO/CPKO may be approved (step 606) for refining, and the certified CPO/CPKO entered into the refinery.

The barcode test results, such as, for example, the test results may be used to match the taggant that was provided to the mill by the refinery, ensuring that the product was provided by the mill. The adulteration (e.g., concentration) tests may be matched between the mill (origin) and refinery (destination). The mass balance results, such as the RSPO results, may be reconciled between the CPO/CPKO that left the mill and the CPO/CPKO that entered the refinery, providing a further certification point, such as, for the example of palm oil, RSPO certification point 636. Data 644 to verify mill compliance will have been logged in the blockchain 310 or database, including barcode test results, such as, for example, PCR test results that match with the taggants printed at the mill (possibly by a MiniDART™ system provided by SafeTraces, Inc.), adulteration test results matching the concentration of from the mill, and mass balance results, such as RSPO results that reconcile between CPO/CPKO out of the mill and the CPO/CPKO into the refinery.

Exemplary Validation Testing, Field and Laboratory Results for Palm Oil

On-the-ground tests at an oil palm plantation and mill, as well as laboratory tests, were conducted to validate the new method. Protocols were designed to answer three questions essential to a 100% traceability solution:

"First mile" source assurance: The ability to successfully deliver DNA barcodes under field conditions to correctly identify the harvest location.

Source assurance in liquids: The stability of DNA barcodes in palm oil for the expected shelf life of the product; targets included 6 months for crude palm oil (CPO) and 12 months for refined palm oil (RPO).

Purity assurance: The extent to which DNA barcodes can detect product dilution or substitution.

Traceability starts at the beginning of the "first mile". In order to be considered sustainably sourced, the product must be harvested on land that is being cultivated in accordance with applicable land use requirements for RSPO certification. Mills typically process products, such as fresh fruit bunches (FFBs) within a 50-mile radius of their location, and often include products, such as FFBs from small holder growers. Establishing the exact location of each harvest can provide the information needed to maintain sustainability compliance. First mile traceability involves applying a unique DNA barcode solution to a product, such as FFB stems, using a proprietary tagging device at the geo-located harvest site. This information is associated with the DNA barcode and uploaded to the blockchain at the harvest location via smartphone. The products, such as FFBs, are then sampled at the mill to identify the harvest location and determine if the location is within the certified area.

DNA barcodes (taggants) are shown to have good stability in crude palm oil (CPO) and refined palm oil (RPO). Because DNA barcodes remain on a product, they are formulated to be fully compatible. In addition, they must remain stable under the conditions that the product will encounter, and for the expected duration of such conditions. To validate DNA barcode stability for palm oil, DNA barcodes were added to CPO and to RPO and maintained at 55 degrees centigrade (° C.) for a period of 8 weeks. The primary purpose of elevating the temperature to this level was to accelerate any potential DNA barcode degradation within these matrices by a factor of 12. That is, results of the 8-week test provide the equivalent degradation that would occur in nearly 2 years at ambient temperature.

The stability index for each sample is shown in FIG. 8 for each test interval in terms of day equivalent, ambient temperature. Results show that the stability index value remained nearly constant for the entire test period, indicating that DNA barcodes are suitable to provide on-product verification within the timeframe that CPO or RPO are in transit between supply chain processing steps.

DNA barcodes (taggants) can also be validated for purity assurance. A method under development to detect product purity while in transit was tested and can currently reliably detect adulteration into the 30% range; a recalibration of the method will allow it to reliably detect adulteration to an operationally sufficient 15% range. The method involves tagging the product with a unique DNA barcode at the point of origin and taking a reference sample that is recorded on the blockchain and sent to the destination. At the destination, a quantitative method (patent pending) compares the DNA barcode concentration in the reference sample to a new sample taken when the product arrives. If both sample test results match within the margin of error, no dilution or substitution occurred while the product was in transit, guaranteeing purity at the destination.

The validation test involved tagging CPO with a unique DNA barcode. Untagged oil was then added to produce 25-milliliter (ml) aliquots of "adulterated" oil. The adulteration percent increased by 10% increments, from 0 to 40%. Each dilution set included 80 samples, for a total of 400 samples.

Results show that the current method detects adulteration levels in the 30% to 40% range with 95% confidence. The recalibration of the method will address overlapping signals to yield precise results for lower levels of adulteration.

Exemplary Process for Palm Oil Traceability

Step 1. Mill-centric harvest management.

For the example of palm oil, the mill is the center of operations for establishing the essential first link that locks the empirical evidence that ensures raw material supply compliance to the blockchain. The daily routine involves a pickup from the mill of newly dispensed DNA barcode and a tagging device for each harvest crew. The dispensed DNA barcode volume is calibrated to match the day's harvest plan, and the DNA barcode and amount is recorded on the blockchain. (Tagging devices are returned to the mill for maintenance and recharging at the end of the shift.)

Step 2. "First mile" traceability.

At the harvest site, each FFB is tagged with a predetermined amount of the assigned DNA barcode. The tagging device is connected to a smartphone that authenticates the user and records the location and time of each tagging operation on the blockchain. If the harvested material exceeds the daily harvest plan due to favorable harvest conditions, the crew notifies the mill to set the stage for a possible favorable exemption.

The tagging device prints the packing slip once the harvest is collected, which the aggregator or collector then delivers to the mill.

As each load is delivered to the mill, packing slips are scanned so the delivered quantity can be reconciled with the amount of DNA barcode issued to each harvesting crew.

If the number of FFBs delivered significantly exceeds the daily harvest plan—which was the basis for the amount of DNA barcoding solution issued—the lot may be rejected unless the harvesting crew notified the mill of a favorable exemption that can be accounted for. This can prevent the delivery of non-conforming product.

Conformity is also achieved through a sampling plan. The system tracks loads and notifies the receiving crew when FFBs should be sampled and tested to achieve the required level of confidence for incoming product conformance Under normal operating conditions, automated sample processing and test equipment will sample and test several hundred FFBs per day and record test results on the blockchain.

Step 3. "Second mile" traceability, from the first CPO destination back to the mill.

Because FFB milling is a continuous process, it is impractical—and perhaps impossible—to identify with 100% precision the exact origin of each CPO lot. However, it is possible to establish a link to the origin of FFBs delivered to the mill on any given day. Since CPO is generally held at a mill for no more than 24 to 48 hours, it becomes possible to narrow the origin to material that met conformity requirements during that period.

For each CPO lot that is to be tracked during shipment, a new DNA barcode is dispensed at the mill, recorded on the blockchain, and applied directly to the CPO at a fixed rate as the oil is loaded onto the transport vehicle. This ensures complete mixing. Since the average CPO yield for FFBs is known, the system has the data needed to perform a mass balance for the number of FFBs delivered and amount of oil to be shipped. This additional data supports a compliance claim. The mill must resolve any notable discrepancies to avoid a potential quarantine order or shipping delays.

Step 4. Source and purity assurance, first destination.

In addition to source assurance, DNA barcodes can provide purity assurance. Extracting a 50 ml "ship-ahead" CPO sample and sending it to the destination in a tamper-proof container provides a reference sample for comparison once the shipment arrives. The verification method accounts for minor variations in the DNA barcode application rate and any low-level degradation that may occur between the time a barcode is applied and when it is tested.

The system can initiate this process by generating a sample ID that is recorded on the blockchain for future reference.

Once the CPO reaches its first destination it is sampled, tested, and compared to the ship-ahead sample to verify the source in accordance with the bill of lading or manifest. The purity can also be tested; adulteration of 15% or more can be detected with 95% confidence level. All results can be recorded on the blockchain.

Whenever multiple lots are consolidated, such as on a large vessel or at the first refinery, a new DNA barcode can be dispensed and applied to the consolidated lot. A new reference sample must be collected, and the tracking process repeats as described above.

Step 5. Additional supply chain nodes.

A new unique DNA barcode can be added to provide traceability and purity assurance along any two nodes along the supply chain as described above.

Step 6. Branded product.

The quality assurance process can be repeated to traces all process steps, inclusive of the branded product.

Figure 7:
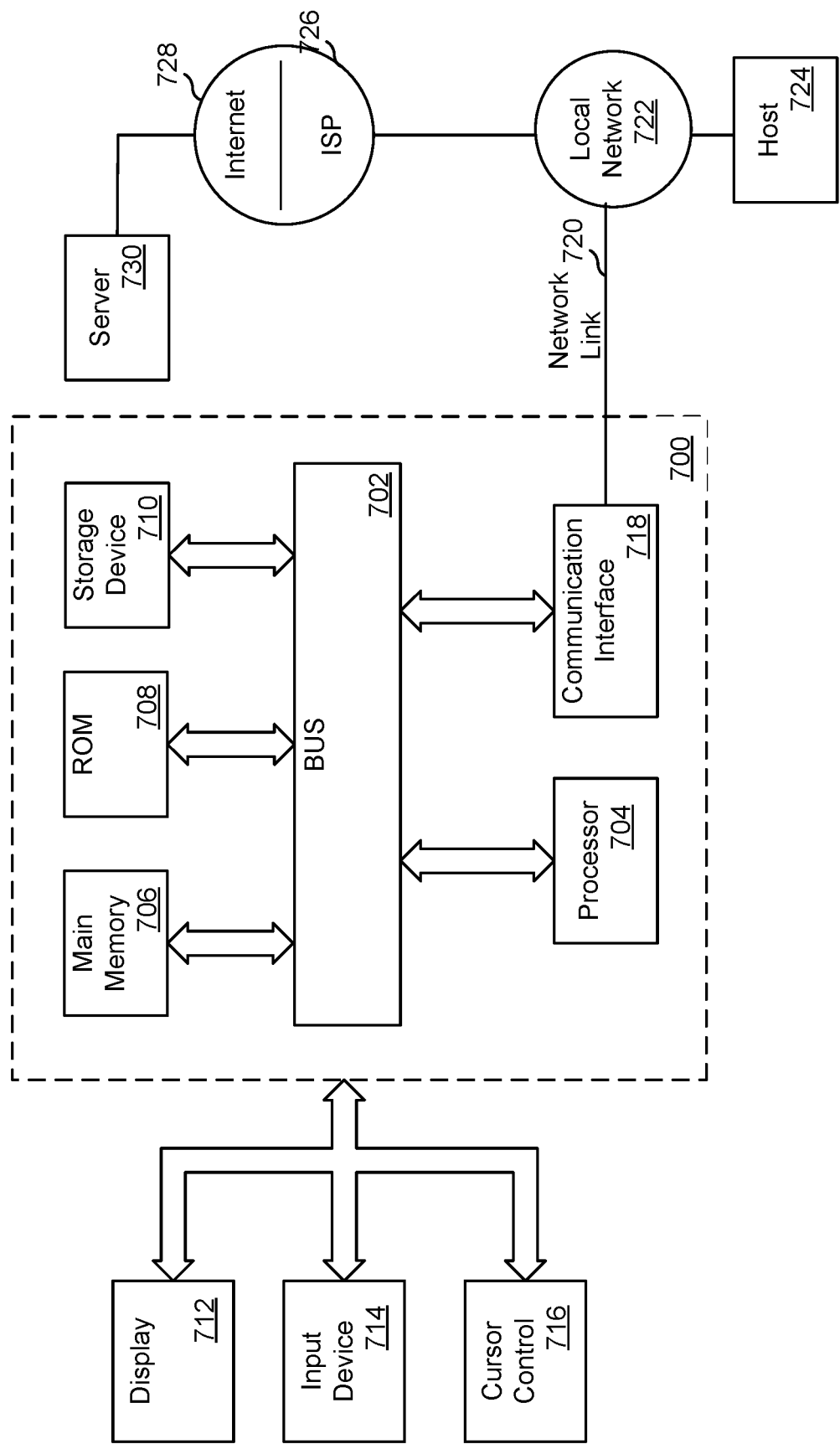
FIG. 7 is a block diagram that illustrates a computer system upon which an embodiment of the invention may be implemented.

The exemplary methods, process, and systems described in the above examples may use a computer system for tracking the product as well as for updating the blockchain. For example, FIG. 7 is a block diagram that illustrates a computer system 700 upon which an embodiment of the invention may be implemented. Computer system 700 includes a bus 702 or other communication mechanism for communicating information, and a processor 704 coupled with bus 702 for processing information. Processor 704 may be, for example, a general purpose microprocessor.

Computer system 700 also includes a main memory 706, such as a random access memory (RAM) or other dynamic storage device, coupled to bus 702 for storing information and instructions to be executed by processor 704. Main memory 706 also may be used for storing temporary variables or other intermediate information during execution of instructions to be executed by processor 704. Such instructions, when stored in non-transitory storage media accessible to processor 704, render computer system 700 into a special-purpose machine that is customized to perform the operations specified in the instructions.

Computer system 700 further includes a read only memory (ROM) 708 or other static storage device coupled to bus 702 for storing static information and instructions for processor 704. A storage device 710, such as a magnetic disk or optical disk, is provided and coupled to bus 702 for storing information and instructions.

Computer system 700 may be coupled via bus 702 to a display 712, such as a computer monitor, for displaying information to a computer user. An input device 714, including alphanumeric and other keys, is coupled to bus 702 for communicating information and command selections to processor 704. Another type of user input device is cursor control 716, such as a mouse, a trackball, or cursor direction keys for communicating direction information and command selections to processor 704 and for controlling cursor movement on display 712. This input device typically has two degrees of freedom in two axes, a first axis (e.g., x) and a second axis (e.g., y), that allows the device to specify positions in a plane.

Computer system 700 may implement the techniques described herein using customized hard-wired logic, one or more ASICs or FPGAs, firmware and/or program logic which in combination with the computer system causes or programs computer system 700 to be a special-purpose machine. According to one embodiment, the techniques herein are performed by computer system 700 in response to processor 704 executing one or more sequences of one or more instructions contained in main memory 706. Such instructions may be read into main memory 706 from another storage medium, such as storage device 710. Execution of the sequences of instructions contained in main memory 706 causes processor 704 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage device 710. Volatile media includes dynamic memory, such as main memory 706. Common forms of storage media include, for example, a floppy disk, flexible disk, hard disk, solid state drive, magnetic tape, or any other magnetic data storage medium, a CD-ROM, any other optical data storage medium, any physical medium with patterns of holes, a RAM, a PROM, an EPROM, a FLASH-EPROM, an NVRAM, or any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 702. Transmission media can also take the form of acoustic or light waves, such as those generated during radio-wave and infra-red data communications.

Various forms of media may be involved in carrying one or more sequences of one or more instructions to processor 704 for execution. For example, the instructions may initially be carried on a magnetic disk or solid state drive of a remote computer. The remote computer can load the instructions into its dynamic memory and send the instructions over a network connection. A modem or network interface local to computer system 700 can receive the data. Bus 702 carries the data to main memory 706, from which processor 704 retrieves and executes the instructions. The instructions received by main memory 706 may optionally be stored on storage device 710 either before or after execution by processor 704.

Computer system 700 also includes a communication interface 718 coupled to bus 702. Communication interface 718 provides a two-way data communication coupling to a network link 720 that is connected to a local network 722. For example, communication interface 718 may be an integrated services digital network (ISDN) card, cable modem, satellite modem, or a modem to provide a data communication connection to a corresponding type of telephone line. Wireless links may also be implemented. In any such implementation, communication interface 718 sends and receives electrical, electromagnetic or optical signals that carry digital data streams representing various types of information.

Network link 720 typically provides data communication through one or more networks to other data devices. For example, network link 720 may provide a connection through local network 722 to a host computer 724 or to data equipment operated by an Internet Service Provider (ISP) 726. ISP 726 in turn provides data communication services through the world wide packet data communication network now commonly referred to as the "Internet" 728. Local network 722 and Internet 728 both use electrical, electromagnetic or optical signals that carry digital data streams. The signals through the various networks and the signals on network link 720 and through communication interface 718, which carry the digital data to and from computer system 700, are example forms of transmission media. Computer system 700 can send messages and receive data, including program code, through the network(s), network link 720 and communication interface 718. In the Internet example, a server 730 might transmit a requested code for an application program through Internet 728, ISP 726, local network 722 and communication interface 718. The received code may be executed by processor 704 as it is received, and/or stored in storage device 710, or other non-volatile storage for later execution.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Conjunctive language, such as phrases of the form "at least one of A, B, and C," or "at least one of A, B and C," unless specifically stated otherwise or otherwise clearly contradicted by context, is otherwise understood with the context as used in general to present that an item, term, etc., may be either A or B or C, or any nonempty subset of the set of A and B and C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present.

The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

Further embodiments can be envisioned to one of ordinary skill in the art after reading this disclosure. In other embodiments, combinations or sub-combinations of the above-disclosed invention can be advantageously made. The example arrangements of components are shown for purposes of illustration and it should be understood that combinations, additions, re-arrangements, and the like are contemplated in alternative embodiments of the present invention. Thus, while the invention has been described with respect to exemplary embodiments, one skilled in the art will recognize that numerous modifications are possible.

For example, the processes described herein may be implemented using hardware components, software components, and/or any combination thereof. The specification and drawings are, accordingly, to be regarded in an illustrative rather than a restrictive sense. It will, however, be evident that various modifications and changes may be made thereunto without departing from the broader spirit and scope of the invention as set forth in the claims and that the invention is intended to cover all modifications and equivalents within the scope of the following claims.

All references, including publications, patent applications, and patents, cited herein are hereby incorporated by reference to the same extent as if each reference were individually and specifically indicated to be incorporated by reference and were set forth in its entirety herein.

What is claimed is:

1. A method of tracking a material in a supply chain comprising:
   securely recording an application location, wherein the application location is a geolocatable production location at which at an application device applies a DNA taggant set to a first batch of the material produced by a first supplier of the material, the DNA taggant set corresponding to a tag string corresponding to the first supplier;
   receiving the first batch at a processing facility;
   determining a geographic coordinate of the geolocatable production location;
   comparing the application location to the geographic coordinate;
   selecting a sample from the first batch if the application location matches the geographic coordinate; and
   testing the sample to determine a sampled DNA taggant set.

2. The method of claim 1, wherein the DNA taggant set comprises a taggant material including at least N unique pieces of DNA, representing N digits of a barcode that identifies the first batch of the material and is associated with the tag string, N being a positive integer greater than 1, wherein each of the at least N unique pieces of DNA represents one value of a corresponding one of the N digits, the method further comprising:
   detecting detected pieces of DNA applied to the first batch of the material;
   deriving a derived barcode from the detected pieces of DNA; and
   comparing the derived barcode to a predetermined barcode that identifies the first batch of the material.

3. The method of claim 1, wherein the DNA taggant set is applied by spraying with the application device and the application device is capable of applying multiple DNA taggant sets.

4. The method of claim 3, further comprising:
   selecting a plurality of DNA taggants to determine the DNA taggant set.

5. The method of claim 4, further comprising:
   after applying the DNA taggant set to the first batch of the material, selecting a second plurality of DNA taggants to determine a second DNA taggant set and applying the second DNA taggant set to a second batch; and
   receiving the second batch at the processing facility.

6. The method of claim 1, further comprising labeling the sample selected from the first batch with a grade and associating the grade with the tag string.

7. The method of claim 1, wherein the DNA taggant set includes at least N unique specific target fragments of synthetic DNA, wherein each of the at least N unique specific target fragments of synthetic DNA corresponds to a first binary value of zero or a second binary value of one.

8. The method of claim 1, further comprising:
   recording a time at which the application device applies the DNA taggant set to the first batch of the material; and
   verifying that the time is within an expected time range.

9. A method of tracking a batch of a product from a geographically defined location to a processing location:
   providing an application device with an amount of issued DNA taggant set, based on an estimated amount of the product to be harvested from the geographically defined location;
   applying, to the batch of the product, an applied DNA taggant set with the application device, wherein the applied DNA taggant set is from the amount of the issued DNA taggant set, thereby forming a tagged batch of the product with the applied DNA taggant set applied thereon;
   delivering the tagged batch to the processing location;
   determining an expected tag sequence for the tagged batch based on tag records; and
   sampling the tagged batch to identify the applied DNA taggant set applied thereon;
   comparing the expected tag sequence for the tagged batch to the applied DNA taggant set applied thereon.

10. The method of claim 9, wherein the application device tracks a number of actuations, each actuation indicating issued DNA taggant set was dispensed.

11. The method of claim 10, wherein the application device tracks a geographic location of a particular actuation.

12. The method of claim 11, wherein the geographic location and a time of the particular actuation is stored, the method further comprising:
   comparing the geographic location and the time of the particular actuation to an expected location and expected time.

13. The method of claim 10, wherein the application device is wirelessly connected to a cellular device, the application device communicating the number of actuations to the cellular device.

14. The method of claim 9 wherein a given DNA taggant set, of issued DNA taggant sets and/or applied DNA taggant sets, comprises a taggant material including at least N unique pieces of DNA, representing N digits of a first barcode, N being a positive integer greater than 1, wherein each of the at least N unique pieces of DNA represents one value of a corresponding one of the N digits, and verifying the applied DNA taggant set comprises:
  detecting applied pieces of DNA from the given DNA taggant set, as applied;
  deriving a derived barcode from the applied pieces of DNA; and
  comparing the derived barcode to the first barcode corresponding to the given DNA taggant set.

15. The method of claim 9, further comprising:
  processing the product to produce a liquid;
  adding a second DNA taggant set to the liquid;
  moving the liquid to a new location; and
  sampling the liquid for a sample DNA taggant set to verify a second barcode of the sample DNA taggant set matches a barcode corresponding to the second DNA taggant set and matches an expected concentration of the second DNA taggant set.

16. A method of tracking a product from a geographically defined origination location to a processing facility using a DNA taggant set comprising a taggant material including at least N unique pieces of DNA, representing N digits of a barcode, N being a positive integer greater than 1, wherein each of the at least N unique pieces of DNA represents one value of a corresponding one of the N digits, the method comprising:
  estimating an estimated amount of issued DNA taggant set based on an estimated amount of product to be produced at the geographically defined origination location;
  issuing a sprayer containing the estimated amount of issued DNA taggant set, the issued DNA taggant set having a corresponding issued barcode;
  applying, by actuating the sprayer, the issued DNA taggant set to the product, the sprayer tracking a time and a location of an actuation of the sprayer by storing the time and location in a database;
  verifying the location is within the geographically defined origination location;
  verifying the time is within an expected time range;
  delivering the product to a processing location, with an applied DNA taggant set; and
  verifying that a corresponding barcode corresponding to the applied DNA taggant set matches an issued barcode of the issued DNA taggant set.

17. The method of claim 16, wherein the sprayer uses a cellular device to transmit the time and the location.

18. The method of claim 17, wherein the sprayer is connected to the cellular device using a Bluetooth connection.

19. The method of claim 16, wherein the product is palm fruit and the processing location is a mill that issues the sprayer.

* * * * *